United States Patent [19]

Munro

[11] Patent Number: 4,990,089
[45] Date of Patent: Feb. 5, 1991

[54] METHOD AND MATERIAL FOR BRIGHTENING TEETH

[75] Inventor: John R. Munro, Crossville, Tenn.

[73] Assignee: Dunhall Pharmaceuticals, Inc., Gravette, Ark.

[21] Appl. No.: 519,318

[22] Filed: May 4, 1990

Related U.S. Application Data

[63] Continuation of Ser. No. 235,304, Aug. 23, 1988, abandoned.

[51] Int. Cl.$^5$ ............................................. A61C 5/00
[52] U.S. Cl. ................................................... 433/215
[58] Field of Search ...................... 433/80, 203.1, 215, 433/216; 424/53

[56] References Cited

U.S. PATENT DOCUMENTS

| | | | |
|---|---|---|---|
| 2,257,709 | 9/1941 | Anderson | 433/215 |
| 3,073,300 | 1/1963 | Berghash | 128/136 |
| 3,247,844 | 4/1966 | Berghash | 128/136 |
| 3,448,738 | 6/1969 | Berghash | 128/136 |
| 3,527,219 | 9/1970 | Greenberg | 433/215 |
| 3,624,909 | 12/1971 | Greenberg | 433/80 |
| 3,657,413 | 4/1972 | Rosenthal | 424/81 |
| 3,998,945 | 12/1976 | Vit | 424/53 |
| 4,064,628 | 12/1977 | Weitzman | 433/80 |
| 4,302,441 | 11/1981 | Muhlemann et al. | 424/48 |
| 4,428,373 | 1/1984 | Seid et al. | 433/80 |
| 4,431,631 | 2/1984 | Clipper et al. | 424/53 |
| 4,522,805 | 6/1985 | Gordon | 424/52 |
| 4,537,778 | 8/1985 | Clipper et al. | 424/53 |
| 4,592,487 | 6/1986 | Simon et al. | 222/94 |
| 4,592,488 | 6/1986 | Simon et al. | 222/94 |
| 4,770,634 | 9/1988 | Pellico | 433/215 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |

OTHER PUBLICATIONS

Bleaching Tetracycline Stains by Richard M. Zillich, DDS, Continuing Education Article, #2, vol. V, No. 6, Jun. 1984, p. 465.

Primary Examiner—Cary E. Stone
Attorney, Agent, or Firm—Frijouf, Rust & Pyle

[57] ABSTRACT

There is disclosed a process and a material for brightening teeth. The process comprises the construction of a splint around the tooth or teeth to be brightened, followed by the insertion within the splint of a brightening agent selected from one of many peroxide groups. The splint is constructed so that the splint is relatively liquid tight to the gingiva. The brightening agent is periodically renewed and can be mixed with various other agents to increase the nascent oxygen release aerating factors. In one embodiment, the peroxide that is used is a 10% solution of carbamide peroxide mixed with a water free gel.

16 Claims, 2 Drawing Sheets

METHOD AND MATERIAL FOR BRIGHTENING TEETH

This application is a continuation of application Ser. No. 235,304, filed Aug. 23, 1988, now abandoned.

FIELD OF THE INVENTION

This invention relates to a brightening agent and process for brightening teeth, and more particularly to such a process that is user activated and controlled.

DESCRIPTION OF PRIOR ART

There is no need to dwell on the cosmetic desires of people to have bright teeth. Over the years many processes have come and gone, each promising a new breakthrough in teeth brightening. In general, the processes that work are too costly to use, or require special training or are harsh on the teeth.

Since tooth stains stem from a large variety of causes, from poor oral hygiene to the use of drugs (such as tetracycline), to the smoking of tobacco products, a universal solution has evaded dentistry. One process for brightening the stains caused by tetracycline is shown in the Copendium of Continuing Education (Endodontal) Vol. V, No. 6, June 1984, page 465. This multi-page brochure outlines the steps a trained professional should take to perform the process of brightening stained teeth. The results of this process are mixed at best. The Compendium which is hereby incorporated by reference, contains a discussion of teeth bleaching techniques, all of which require the application of heat.

The tooth brightening processes available today rely upon some physical manipulation of the teeth. The process described in the above-mentioned publication is one example. Another example is the use of bonding to cover stained teeth. A common step in all such processes is that a trained professional must perform every step of the process. It is the professional who controls the ultimate color of the teeth and not the patient.

Thus, it is clear that a need exists in the art for a product and process that can be used safely by any person and whereby the user can control the degree of brightness of the teeth.

A further need exists in the art for a process of tooth brightening, coupled with a system for protecting the brightened teeth from reverting back to their original dull or stained appearance, the entire system being under control of the user.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

I have discovered that peroxide compounds, which have been commercially available for a number of years and used by professionals and others for a wide variety of purposes have an unexpected result when used in a very specific manner.

While it is true that hydrogen peroxide has been known for years to act as a cleanser for teeth, it is also true that the rapid decomposition of hydrogen peroxide has limited its usefulness. Indeed, the procedure discussed above for cleansing tetracycline stains takes into account this well-known deficiency of hydrogen peroxide.

The commercial product PROXIGEL, described in U.S. Pat. No. 3,657,413 issued on Apr. 18, 1972 to M. W. Rosenthal, which patent is hereby incorporated herein by reference, is one attempt to overcome the problems of hydrogen peroxide by using urea peroxide in a slowly dispersable glycerol based solvent. This combination, according to the above-mentioned patent, improves sustained nascent oxygen release. It is the nascent oxygen release which is believed to cause the antiseptic and/or cleansing effect of the peroxide. PROXIGEL, which is manufactured by Reed & Carnrick, is a 10% solution of carbamide peroxide in a water free gel base.

The problem with peroxides is well stated in the Rosenthal patent as follows:

The principal limitation of commonly used peroxide aqueous solutions, however, is their brief period of contact and function an oral tissues. Since many oral bacteria, as well as saliva, contain high concentrations of the enzyme catalase and other peroxides, the hydrogen peroxide is rapidly decomposed into gaseous oxygen and water. It is a well known fact that the antibacterial effects of peroxide are exercised only at the instant that the peroxide decomposes to release nascent oxygen. The gaseous oxygen molecules subsequently formed by combination of the nascent oxygen atoms have no antibacterial effects or tissue oxygenating potential. Thus, there is only transitory contact of the active oxygenating agent with the affected tissues. Furthermore, the low viscosities of water solutions of hydrogen peroxide itself and the water solutions of hydrogen peroxide-active salts, do not allow the active material to stay in contact with affected tissues for as long as is desirable because of the constant flushing effects of salivary secretions. This tendency toward rapid decomposition of $H_2O_2$ into gaseous oxygen and water and the rapid removal of peroxide solutions has severely limited their application to, and utility on, oral tissues.

It would be highly desirable, therefore, to extend the period of oxygen release from hydrogen peroxide for considerably longer periods, as well as to increase the period of retention on tissues.

The Rosenthal patent then goes on to describe a gel form of the peroxide to allow longer action of the peroxide. The purpose of the Rosenthal product is for tissue cleansing and antiseptic use. Subsequent patents, such as U.S. Pat. No. 4,431,631 and 4,537,413, issued Feb. 14, 1984 and Aug. 27, 1986, respectively, deal with the same problem and solve it by creating various aerating gels for longer adherence to the tissue.

In contrast to the prior art, the process of this invention begins with a professional making a splint for the user. The splint is, advantageously, made from a clear, very thin plastic material and is designed to extend onto the user's gingiva and to fit tightly thereto so as to minimize air or saliva from impacting the enclosed teeth. The splint is designed to fit one or more teeth as desired. The user then places a drop or two of the cleanser solution such as the peroxide based PROXI- GEL solution discussed above) into the splint and places the splint, with the solution inside, around the tooth or teeth and over a portion of the gingiva.

The patient then wears the splint for a number of hours, removes the splint, rinses the teeth, preferably with a fluoride compound, and then, repeats the process. Those users who wish to brighten their teeth slowly will wear the splint only while sleeping. This method will usually take about four weeks to show dramatic results. Others, who desire faster whitening, may choose to wear the splint during the day as well. This is possible because of the transparent, thin nature of the splint. When the degree of brightness desired by the user is achieved, the user stops using the splint.

The tightly fitting splint serves the dual purpose of physically restraining the solution from evaporating or migrating away from the teeth, and also preventing the destruction of the oxygenating properties of the peroxide. Dramatic results have been demonstrated with this procedure.

Thus, it is a feature of my invention to have a professional prepare for the user a splint designed to tightly fit around the tooth or teeth to be brightened, have the user place a solution of peroxide within the tooth cavity formed in the splint and then to insert the splint around the proper tooth or teeth. The user then periodically replenishes the peroxide and repeats the process until the desired amount of brightness is achieved.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be head to the following detailed description taken in connection with the accompanying drawings in which.

Similar reference characters refer to similar parts throughout the several views of the drawings.

DETAILED DISCUSSION

Figure 1:
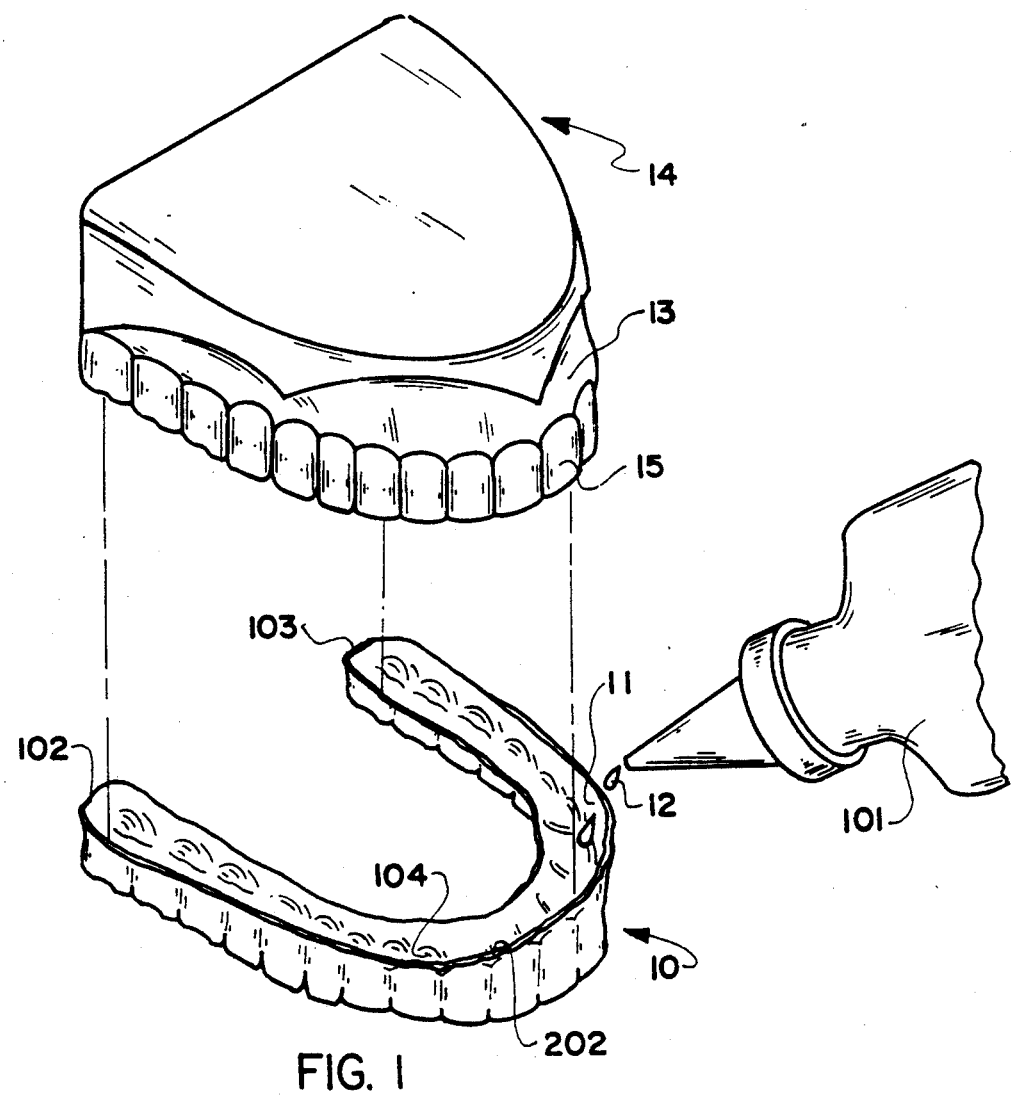
FIG. 1 shows a set of upper teeth and a full splint therefore.

FIG. 1 illustrates a mold 14 a full tooth mold made in a traditional way by the dentist. In this discussion, we can assume that mold 14 is in fact a representation of the actual mouth of a patient having gingiva 13 with teeth 15 extending therefrom. Of course, in our example mold 14 contains all of its teeth. This, as will be seen, is not necessarily critical to the functioning of the invention. In addition, many people have teeth which are not fully aligned. This again, is not a problem, since the splint, (as will be discussed) will allow for individual tooth differences. FIG. 1 also shows splint 10 made by the dental professional in a manner to be more fully detailed hereinafter. At this point, it is sufficient to note that splint 10 has sealed end portions 102 and 103 and inter proximal portions 104 within the splint 10. The person wishing to brighten his or her teeth obtains the cleaning solution 101 (which will be discussed in more detail hereinafter) and places within the tooth cavity 11 of the splint a few drops 12 of the solution.

Figure 2:
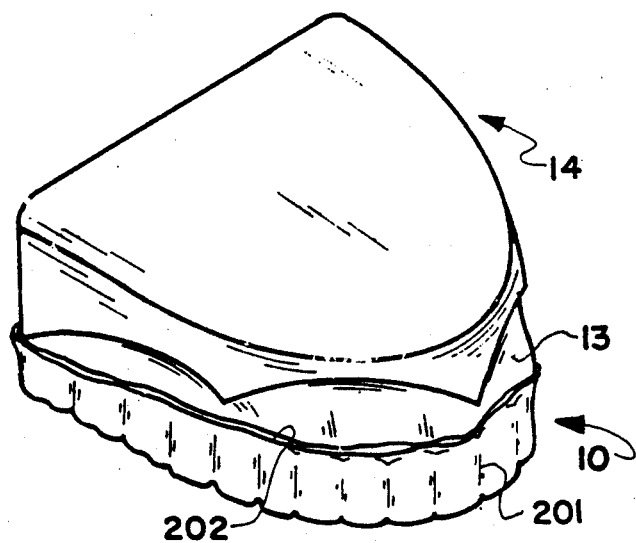
FIG. 2 shows the splint positioned on the teeth.

As shown in FIG. 2, the splint is then positioned by the user around teeth 15 and gingiva 13 making a substantially air tight seal 202 between the top portion of splint 10 and gingiva 13.

Figure 3:
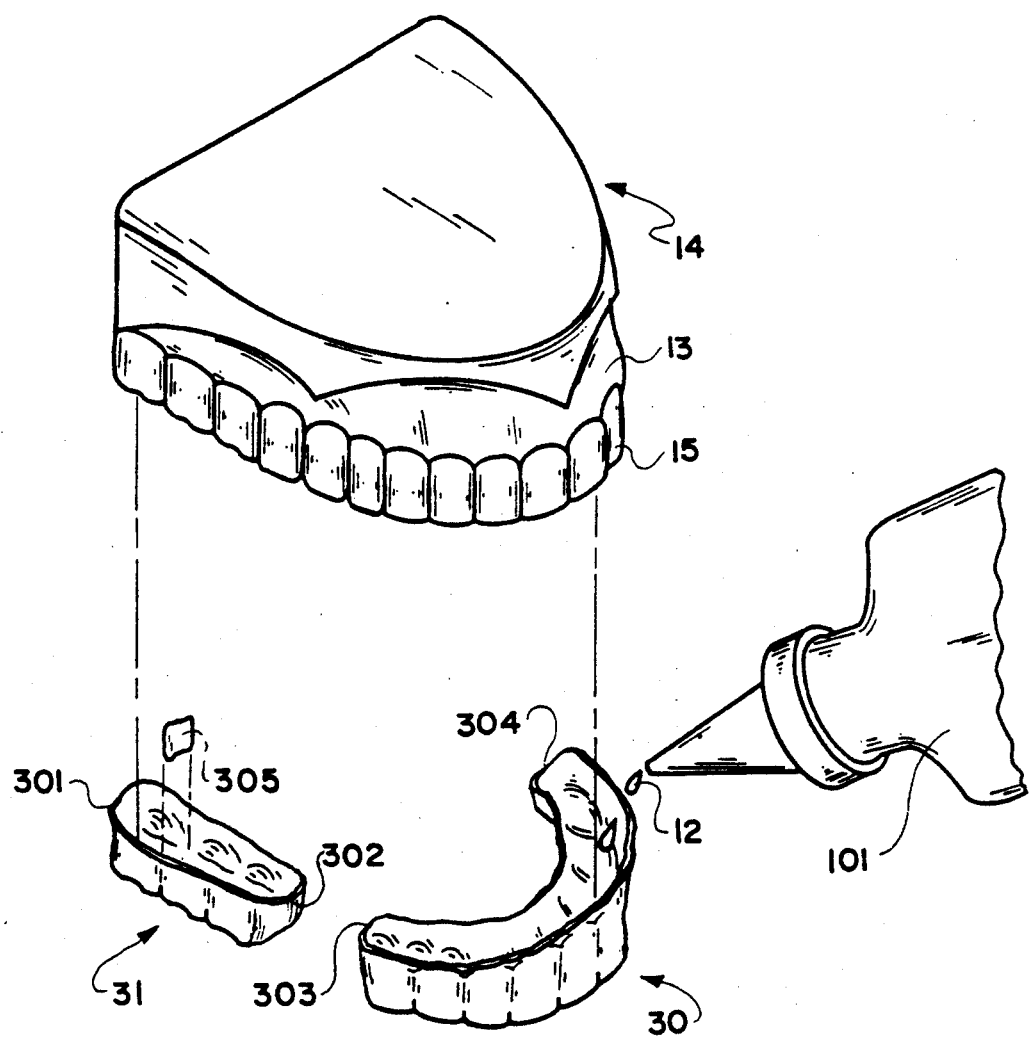
FIG. 3 shows a set of upper teeth and two partial splints therefore; and the two partial splints of FIG. 3 positioned on the teeth.

FIG. 3 shows the same mouth mold 14 with two partial splints 30 and 31. Splint 30 covers some of the front teeth whole splint 31 covers three of the molars. It should be noted the splints 30 and 31 can be constructed to cover any number of teeth, from a single tooth to a full splint. The ends of splint 30 have closed end portions 303 and 304 formed to prevent cleansing solution 12 from leaking out of the splint. Splint 31 has end portions 301 and 302 similarly designed.

Figure 4:
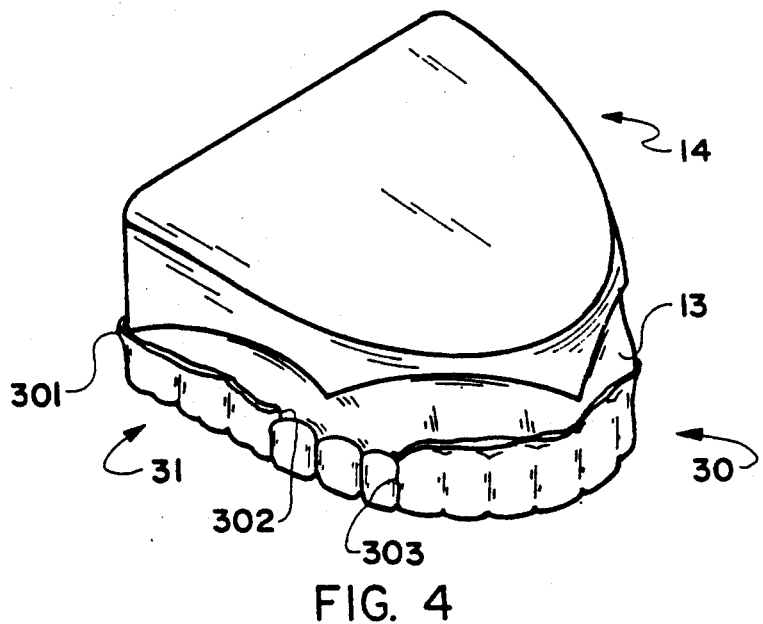

FIG. 4 shows partial splints 30 and 31 positioned around their respective teeth, each forming a substantially air tight seal with their adjacent gingiva.

Once the splint is in place, the user then wears the splint for a number of hours, removes the splint, rinses the teeth, preferably with a fluoride compound, and then repeats the process. For users who wish to brighten their teeth slowly, wearing the splint only while sleeping will suffice. This method will usually take about four weeks to show dramatic results. Others, who desire faster whitening, may choose to wear the splint during the day as well. This is possible because of the transparent, thin nature of the splint. When the degree of brightness desired by the user is achieved, the user stops wearing the splint.

One method of creating the splint includes the following steps:

(a) making a mold of the tooth or teeth to be cleaned in the traditional manner, well-known to dental professionals and as shown in FIG. 1;

(b) obtaining a sheet of plastic material of the appropriate size and between 0.01 inch and 0.1 inch thick depending upon the application;

(c) placing the sheet in a holder;

(d) spraying silicone on both sides of the plastic sheet;

(e) heating the plastic sheet on one side only until it becomes clear;

(f) placing the clear plastic over the prepared model (missing teeth can be replaced with denture teeth or metal crown forms) or over only the teeth representative of the teeth to be cleaned.

(g) immediately pressing molding putty against the heated plastic, using fingers to contour the heated plastic over the model;

(h) removing the model and trimming the plastic; and (i) sealing the ends of the splint to minimize air and saliva from entering and to minimize solution from leaking (or bring sucked) out.

Another method of forming the splint would be to use the omnivac method now commonly employed in dentist offices for other dental applications. It is important to note, however, that any method of constructing a splint is acceptable. Advantageously, the splint should be resilient to allow the user to remove and replace the splint around the tooth or teeth.

The solution that is inserted in the splint can be selected from the peroxy compounds, and can be the above-mentioned PROXIGEL oral cleanser. One drop per tooth has shown to be sufficient to begin the cleaning process. Renewing the solution every 4 hours has shown to be effective in substantially brightening teeth within two weeks to a point where the difference in brightness (before and after) is readily apparent even to the untrained eye. The longevity of the brightness, or to say if the other way, the amount of time it takes for the stains or yellowing to return will depending upon conditions in the mouth.

This procedure has been demonstrated to clean yellow teeth, teeth dark from tetracycline, dark from reaction to orthodontics and teeth dark from unknown causes. In most situations, the compound used was a 10% solution of carbamide peroxide. Tests have shown the preferred cleaning solution to be peroxyl gel mixed with peroxigel in the ratio of 3 millileters of peroxyl gel to 1.2 ounces of peroxyl. Greater than 3 milliliters of peroxyl reduces the viscosity to a point where it is not easily retained in the splint. Stannous fluoride, or other fluorides, can be mixed with the cleaner to provide greater benefits, if desired. Other compounds used with this method have shown good results.

One advantage of this procedure is that the teeth are cleaned uniformly and at the same time. Thus, a person does not have each tooth a different color, even for a few days. This is of particular importance where teeth are misaligned or not straight. The splint holes the cleaning solution against the teeth and even brightening is achieved. Of course, when and if it is observed that one portion of teeth is becoming brighter than another, the splint can be modified to allow different amounts of fluid into contact with different teeth. This can be done with separate splints, or with splints divided into sections internally by physical barriers. The physical barriers can be part of the splint structure or added temporarily for periods of time. This is shown by barrier 305 in FIG. 3. Barrier 305 can be, for example, cemented in position between teeth to allow for separate application of cleansing material in each section. The dental professional can adjust the positioning of the barrier by removing and recementing the barrier, or by other means.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. The process of brightening teeth comprising the steps of:
   obtaining a substantially liquid tight splint to cover the tooth or teeth to be brightened;
   placing within said splint a brightener agent at the location within said splint associated with the tooth surfaces to be brightened; and
   placing the splint containing said brightener agent around the tooth or teeth to be brightened.

2. The process of claim 1 wherein the brightener agent is a nonaqueous oral peroxy compound.

3. The process of claim 2 wherein said brightener agent is mixed with stannous fluoride.

4. The process of claim 2 where said oral peroxy compound is peroxyl gel mixed with peroxigel in the ratio of 3 milliliters of peroxyl to 1.2 ounces of peroxigel.

5. The process of claim 1 further comprising the steps of:
   periodically removing said splint:
   adding additional brightener agent; and
   replacing said splint containing said additional brightener agent around the tooth or teeth to be brightened.

6. The invention set forth in claim 5 wherein said periodically removing step includes the step of obtaining a fresh unused substantially airtight splint to cover the tooth or teeth to be brightened, and wherein said replacing step, includes the step of substituting said fresh splint for said removed splint.

7. The invention set forth in claim 1 where the splint obtaining step includes the steps of:
   making an impression of the tooth or teeth to be brightened, said impression including adjacent gingiva;
   molding said impression to create a mold of said tooth or teeth to be brightened;
   forming plastic tightly around said mold; and
   trimming said formed plastic to fit over said tooth or teeth to be brightened and over said adjacent gingiva.

8. The invention set forth in claim 7 wherein said trimmed plastic is between 0.01 inch and 0.1 inch thick.

9. The invention set forth in claim 7 wherein said trimmed plastic is transparent.

10. The use of a peroxy compound to bleach teeth, where the use consists of:
    bringing said peroxy compound into physical contact with each said tooth to be cleaned;
    creating a mechanical barrier around said peroxy compound after said physical contact is made, said mechanical barrier relying upon intimate contact with the gingiva adjacent the tooth for a substantially airtight and leakproof seal.

11. The use of a peroxy compound as set forth in claim 10 wherein physical contact is made with a plurality of teeth at the same time and wherein said mechanical barrier extends to all of said plurality of teeth.

12. The use of peroxy compound as set forth in claim 11 wherein said mechanical barrier contour provides means for allowing continued physical contact of different amounts of said peroxy compound for different teeth.

13. The use of a peroxy compound as set forth in claim 12 wherein said last mentioned means is adjustable.

14. The use of a peroxy compound as set forth in claim 10 wherein said mechanical barrier is a splint obtained by the steps of:
    making an impression of the tooth or teeth to be brightened, said impression including adjacent gingiva;
    molding said impression to create a mold of said tooth or teeth to be brightened;
    forming plastic tightly around said mold; and
    trimming said formed plastic to fit over said tooth or teeth to be brightened and over said adjacent gingiva.

15. The use of a peroxy compound as set forth in claim 14 wherein said trimmed plastic is transparent.

16. The use of a peroxy compound as set forth in claim 10 wherein said compound is a mixture of peroxyl gel and peroxigel in the ratio of 3 milliliters of peroxyl to 1.2 ounces of peroxigel.

* * * * *

UNITED STATES PATENT AND TRADEMARK OFFICE
CERTIFICATE OF CORRECTION

PATENT NO. : 4,990,089
DATED : February 5, 1991
INVENTOR(S) : John R. Munro

It is certified that error appears in the above-indentified patent and that said Letters Patent is hereby corrected as shown below:

Column 3, line 55, after "splints" (first occurrence) delete "therefore; and the two partial splints".

Column 3, line 61, after "14" insert --shown as--.

Column 4, line 18, delete "whole" and insert therefor --while--.

Column 4, line 63, delete "bring" and insert --being--.

Column 5, line 13, delete "depending" and insert --depend--.

Signed and Sealed this

Thirtieth Day of November, 1993

Attest:

BRUCE LEHMAN

Attesting Officer

Commissioner of Patents and Trademarks